US009866512B2

(12) United States Patent
Brown (10) Patent No.: US 9,866,512 B2
(45) Date of Patent: Jan. 9, 2018

(54) SOCIAL NETWORK COMMUNITIES FOR SUPPORT AND ACCOUNTABILITY BASED ON TRACKED TIPS (75) Inventor: Stephen J. Brown, Woodside, CA (US)

(73) Assignee: Invent.ly, LLC, Woodside, CA (US)

( * ) Notice: Subject to any disclaimer, the term of this patent is extended or adjusted under 35 U.S.C. 154(b) by 1230 days.

(21) Appl. No.: 12/011,843

(22) Filed: Jan. 29, 2008

(65) Prior Publication Data

US 2009/0193082 A1 Jul. 30, 2009

(51) Int. Cl.
G06F 15/16 (2006.01)
H04L 12/58 (2006.01)
G06Q 50/22 (2012.01)
A63B 24/00 (2006.01)
G06F 17/30 (2006.01)
G06Q 10/10 (2012.01)

(52) U.S. Cl.
CPC .......... H04L 51/32 (2013.01); A63B 24/0075 (2013.01); G06Q 50/22 (2013.01); A63B 2024/0065 (2013.01); A63B 2024/0068 (2013.01); A63B 2024/0081 (2013.01); G06F 17/30867 (2013.01); G06Q 10/10 (2013.01); H04L 51/34 (2013.01); Y10S 128/92 (2013.01)

(58) Field of Classification Search
CPC ....... H04L 51/32; H04L 12/588; G06Q 50/22; Y10S 128/92; A63B 24/0075; A63B 2024/0065; A63B 2024/0068; A63B 2024/0081
USPC ....................................................... 709/204
See application file for complete search history.

(56) References Cited

U.S. PATENT DOCUMENTS

| 7,249,123 | B2 | 7/2007 | Elder et al. |
| 2004/0210661 | A1* | 10/2004 | Thompson ................... 709/228 |
| 2008/0040674 | A1* | 2/2008 | Gupta .......................... 715/745 |
| 2008/0086318 | A1* | 4/2008 | Gilley et al. .................... 705/1 |

(Continued)

OTHER PUBLICATIONS

"LifeTips", 2007, LifeTips, pp. 1-1, http://www.lifetips.com/about/get-reading.html.

(Continued)

Primary Examiner — David Lazaro
Assistant Examiner — Xiang Yu
(74) Attorney, Agent, or Firm — Christopher P. Maiorana, PC (57) ABSTRACT Bookmarking content modules and tracking scores of user properties against the bookmarked content modules on a computer implemented social network are provided. Content modules containing text, audio, video, or audio-video content are accessible to users of a social network. User properties are associated with the users of the social network and the user properties are related to the content modules. Each user of the social network can bookmark a content module and score a user property against the bookmarked content module related with the same user property. Scores are tracked over a period of time to provide motivation and accountability to the user. Ad hoc online communities form around the bookmarked content modules; members of an online community all share at least one common bookmarked content module. A messaging function is provided for members of an online community to communicate with each other to foster support and accountability.

2 Claims, 5 Drawing Sheets (56) References Cited

U.S. PATENT DOCUMENTS

2009/0035733 A1* 2/2009 Meitar et al. ................. 434/118
2009/0043789 A1* 2/2009 Gupta ........................... 707/100

OTHER PUBLICATIONS

"Ning—Social Network Features", 2007, Ning, pp. 1-3, http://www.ning.com/about/features.html.
"Ning—About Us", 2007, Ning, pp. 1-2, http://www.ning.com/about/about-us.html.
"Digg / How Digg Works", 2007, pp. 1-2, http://digg.com/how.

* cited by examiner

SOCIAL NETWORK COMMUNITIES FOR SUPPORT AND ACCOUNTABILITY BASED ON TRACKED TIPS

FIELD OF THE INVENTION

The invention relates generally to social bookmarking. More particularly, the present invention relates to tracking user progress associated with content that has been bookmarked by the user.

BACKGROUND

Traditional methods for disseminating guidance include books, videos, and other media created by experts. The impersonal nature and lack of emphasis on motivation and accountability often cause these traditional methods to fail. This is particularly true for expert advice on personal behavioral modifications, such as weight loss. Generally, Internet-based expert services merely place these traditional methods on a digital framework. For the example of weight loss, websites such as eDiets.com and WeightWatchers.com provide tips and articles, written by experts, pertaining to the subject of weight loss and fitness. These Internet services suffer from the same weaknesses as the traditional methods. In particular, online articles and tips written by experts are typically viewed once by a user, discarded, and quickly forgotten. Furthermore, a viewer of the expert advice lacks accurate information on how well the viewer has followed the advice, thereby the efficacy of the expert advice is unknown to the viewer.

Social networks, such as Facebook.com and MySpace.com, provide online communities for members to create and maintain friendships. Typically, a member selects other members to be friends based on pre-existing relationships or user profiles of other members. A member is able to communicate and share online features with the friends. In existing social networks, potential friends sharing a particular interest and/or goal can be difficult to find and require extensive searches.

Traineo.com, DailyStrength.com, and SparkPeople.com are examples of health support websites that attempt to build communities and social networks for health improvement. These health support websites suffer from the same friend-finding difficulties as social networking websites. In addition, health support websites are similar to more traditional methods of advice dissemination in that they provide their users with only limited interaction capabilities with expert advice provided by the website.

Social bookmarking websites, such as Digg.com, provide tools for communities to form based on online material, such as a news story or a blog post. Social bookmarking allows users to tag or label some online content and communicate with other users who have tagged or labeled the same content. The communications are typically limited to comments written on an online bulletin board and no further interaction with the online content is provided.

The present invention addresses at least the difficult problems of personal behavioral modification and social networking.

SUMMARY OF THE INVENTION

The present invention is directed to a computer implemented social network of users capable of bookmarking content modules and tracking user progress related to the bookmarked content modules. An application server operates the social network and a database stores content modules that are accessible by the users of the social network. Each user is associated with one or more user properties and the content modules are related to at least one of the user properties. A user can bookmark one of the content modules, where bookmarking allows the user to retrieve the bookmarked content module and use a scoring function. The scoring function allows the user to make scores of a user property against the bookmarked content module. The scores are tracked and displayed to the user to provide motivation and accountability for the user.

The application server can also maintain a user profile for each of the users of the social network. The content modules can be posted on the user profiles, preferably as a "tip of the day." Preferably, scoring instructions are embedded in the content modules to describe a metric for how user properties should be scored against the content modules. Scoring metrics include binary scoring metrics, numerical range scoring metrics, or any other metric. User properties scored against the content modules can be any behavioral action, emotional state, or any combination thereof. The content modules can be in any format, including text, audio, video, or any combination thereof. Preferably, the social network is for a personal behavioral modification and at least one of the content modules includes coaching content. The content modules can be created and distributed by expert coaches and/or other users of the social network.

The present invention is also directed to forming an ad hoc online community based on bookmarked content modules. The members of an online community have at least one common bookmarked content module. Members of an online community can view the tracked scores of other members and use a message function to communicate with each other to provide support and/or maintain relationships.

BRIEF DESCRIPTION OF THE FIGURES

The present invention together with its objectives and advantages will be understood by reading the following description in conjunction with the drawings, in which.

DETAILED DESCRIPTION OF THE INVENTION

Online content modules can be beneficial to those who view the modules, particularly if the modules contain coaching content. However, consistently following the coaching content in the modules and tracking one's progress based on the modules can be difficult. Below is a detailed description of tracking user property scores against content modules on a computer implemented social network and forming an ad hoc community based on a content module.

Figure 1:
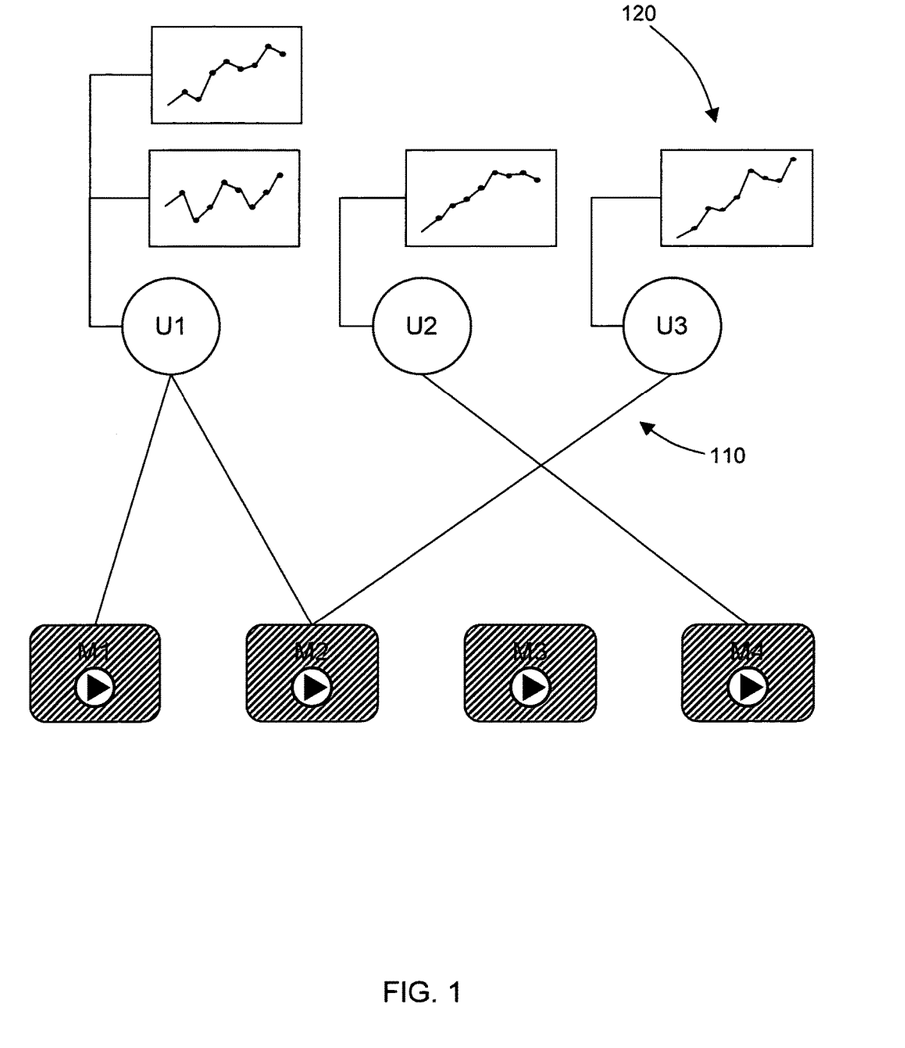
FIG. 1 shows an example of users bookmarking content modules and tracking user scores against the bookmarked modules according to the present invention.

FIG. 1 shows users U1-U3 of a computer implemented social network and content modules M1-M4 accessible by the users U1-U3 of the social network. The computer implemented social network can be for a personal behavioral modification or self-improvement and one or more of the content modules M1-M4 can contain coaching content for helping the users U1-U3 to modify their personal behavior. In FIG. 1, the users U1-U3 can bookmark one or more of the content modules M1-M4, whereby bookmarking enables a user to easily retrieve the content module and score him or herself against the content module. For instance, user U3 has bookmarked 110 content module M2 and has made multiple scores based on or instructed by content module M2 over a period of time. The multiple scores are tracked 120 over all or a part of the same period of time and the progress of user U3 can be charted. Tracking the user scores can be informative for the user to know how well he has followed the bookmarked content module, thereby helping to motivate and hold the user accountable.

It is important to note that each user is associated with user properties and the scores made by a user are based on at least one user property. The content modules are related to the user properties. For example, a content module instructs a user to a limit of one snack per day. A user can make a score based on whether or not he or she exceeded this limit. In another example, a content module instructs a user to participate in physical exercise and the scoring can be on a scale of 0-9 based on the amount of physical exercise undertaken by the user. User properties can include a behavioral action, an emotional state, or any combination thereof. In particular, for a social network for weight loss and fitness, behavioral actions can include amounts of physical exercise, servings of fruits and vegetables consumed, servings of water, and any other activity relevant to weight loss and fitness.

Figure 2:
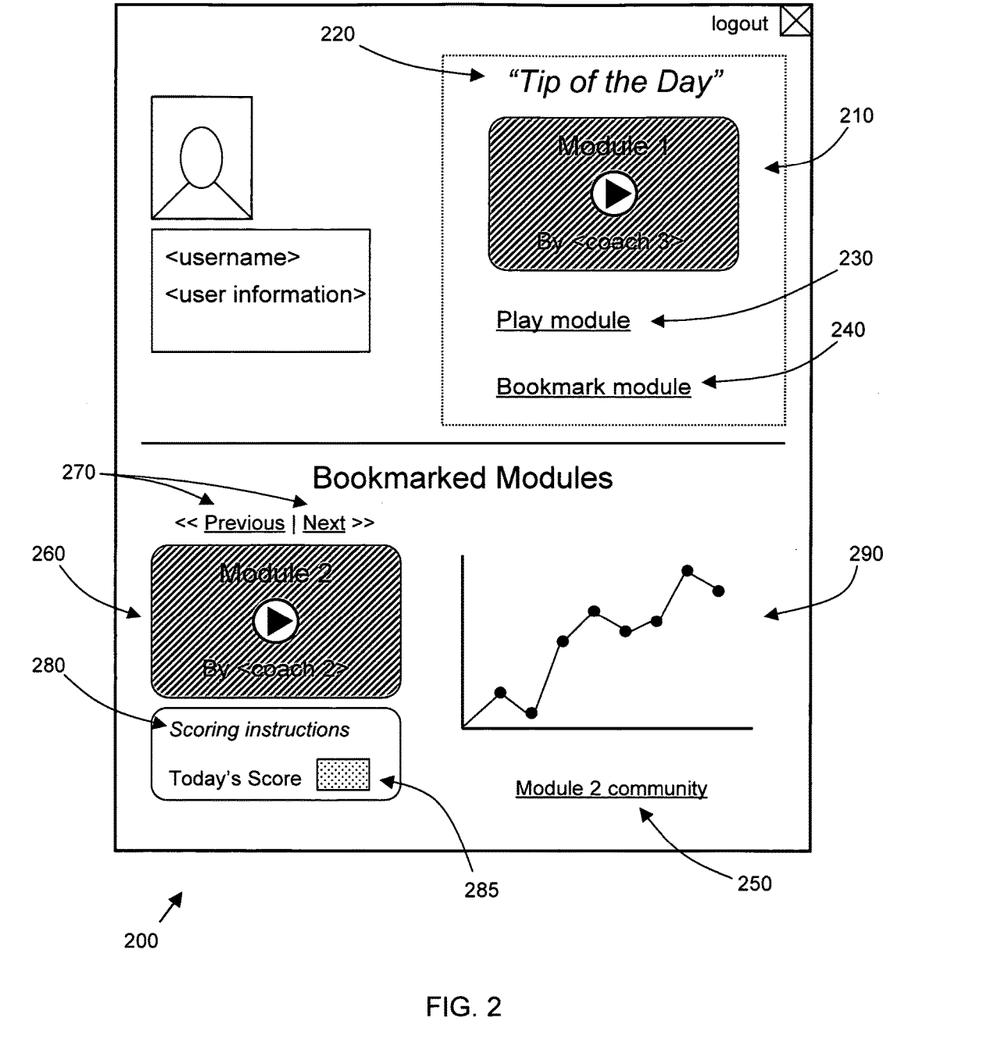
FIG. 2 shows an example of a user profile showing a bookmarked module with scoring and tracking functions according to the present invention.

FIG. 2 shows a preferred embodiment of a user profile 200 of a user of the social network. Preferably, the user profile 200 is viewable on a web browser on a device communicatively connected with a computer network, such as the Internet. A content module 210 is posted on the user profile 200 as a "tip of the day" 220, though any other period of time, such as a "tip of the week", can be used. The user can also access one or more content modules by any other means known in the art, such as weblinks or electronic mail.

The content module 210 can include text, audio, video, audio-video, or any combination thereof. In a preferred embodiment, a content module 210 is a video with coaching content. The video can be played 230 or otherwise viewed by the user. A bookmark function is provided for the user to bookmark 240 the content module. Bookmarking 240 enables the user to retrieve the content module for later viewing. Optionally, bookmarking 240 may also enable the user to download the content module onto the user's personal storage.

The user profile 200 also includes a section for the bookmarked content modules that provides a user interface for scoring and tracking the user scores. A bookmarked content module 260 is shown on FIG. 2. A user can score a user property against the bookmarked module 260 by entering a score in the scoring field 285. Scoring instructions 280 describe how to score a user property against the bookmarked module 260. In a preferred embodiment, each content module has a scoring instruction embedded in the content module, therefore allowing the creator or distributor of the content module to determine the scoring metric for the content module. A scoring metric can be a binary scoring metric, a numerical range scoring metric, or any other metric capable of indicating how well the user has followed the content module. If the content module contains text, audio, video, or audio-video content, the scoring instruction can simply be a part of the content. Optionally or additionally, scoring instructions can be in a separate file accompanying the content module. In an alternative embodiment, the scoring is universal across all content modules.

The user or the content module determines the frequency of calls to the scoring function. Typically, a score can be made on a per day basis. Multiple scores of user properties are tracked for the user to view the progress. A chart 290 of user scores is shown in FIG. 2. Any mechanism for displaying user progress, such as line graphs, bar charts, pie charts, text, etc., can be used. The tracked and displayed scores inform a user how well the user has followed the content module. This may provide motivation and accountability for the user. Generally, a user can bookmark any number of content modules. FIG. 2 shows buttons 270 for accessing other bookmarked modules, though other means, such as a scroll bar or list, may also be employed.

Figure 3:
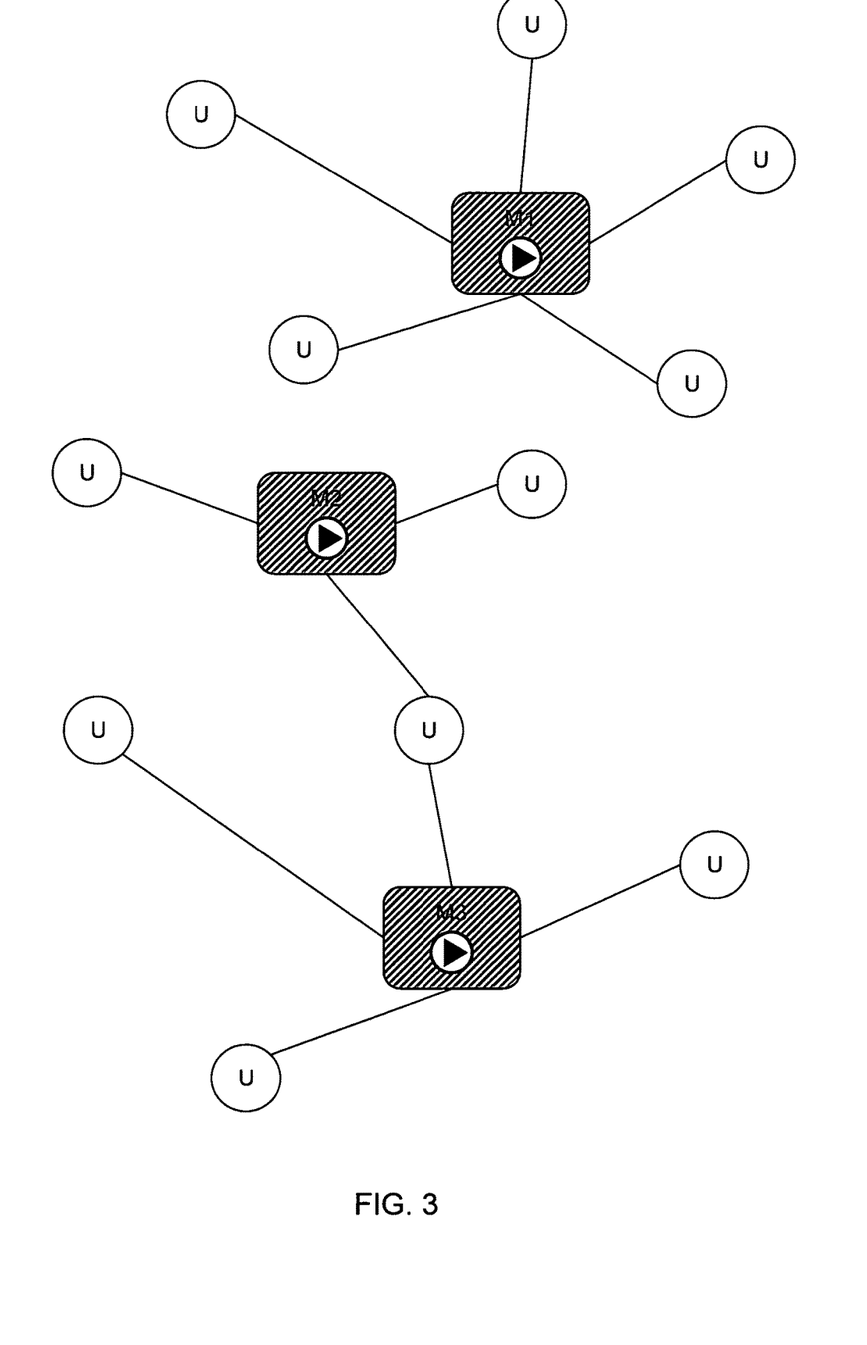
FIG. 3 shows an example of ad hoc communities of users based on content modules according to the present invention.

It is important to note that an ad hoc online community can also be formed based on the bookmarked content modules. FIG. 3 shows communities of users U formed around bookmarked content modules M1-M3. The members of each online community are users U linked together by a community function because they have bookmarked the same content module, and thus, share the same goal dictated by the common bookmarked content module. Since a user can bookmark multiple content modules, the user can belong to multiple communities.

Figure 4:
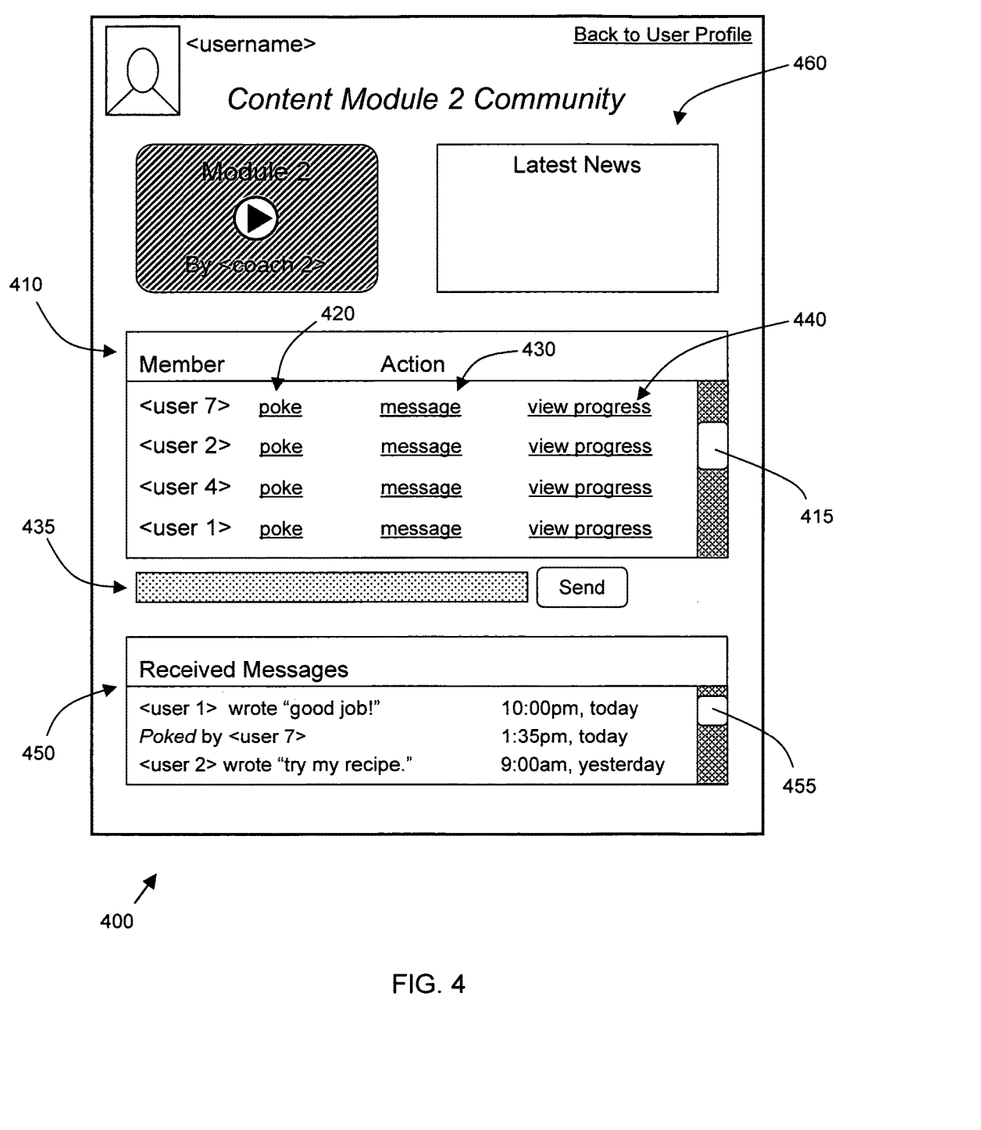
FIG. 4 shows an example of a content module community interface according to the present invention.

In a preferred embodiment, a message function is provided for members of an online community to communicate with each other. FIG. 4 shows an example of a community interface 400 accessible by a community link 250 on the user profile 200 of FIG. 2. Similar to the user profile 200, the community interface 400 is also accessible on a web browser. The community interface 400 can include a list of all members 410 of the community. A community can have any number of members and portions of the list 410 can be accessed by any mechanism, such as a scroll bar 415. A member can view the progress 440 of other members of the community and a message function allows a member to send a message 430 or a poke 420 to another member. The message can be entered in a message text field 435 or can be selected from a list of saved messages. A poke 420 is a short message to simply indicate that the poking member has recently viewed the tracked scores or was thinking about the poked member.

The community interface 400 can also include other features, such as a newsfeed 460 and a textbox for received messages 450. The messaging community fosters motivation and support for the members of the community. Additionally, a member of a community may feel more accountable to follow the bookmarked content module if the progress of the member is viewable by other members of the community.

Figure 5:
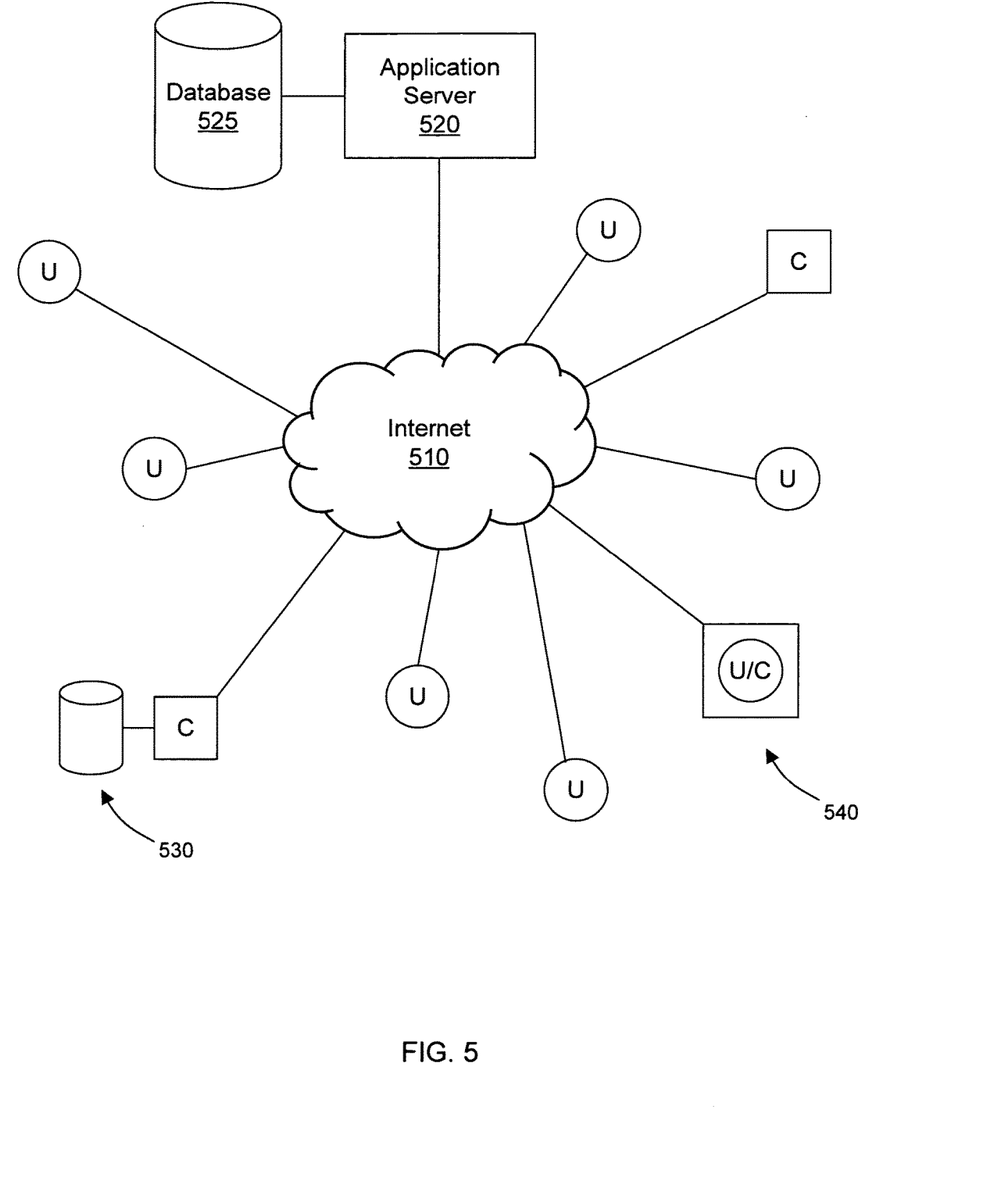
FIG. 5 shows an example of a computer implemented social network of users and coaches according to the present invention.

FIG. 5 shows an example system for operating a social network of users U, associated with user properties, capable of bookmarking content modules and scoring the user properties against the bookmarked content modules. An application server 520 operates a social network of users U who can access the social network and content modules through a computer network, such as the Internet 510. Content modules are created or distributed by coaches C, who may be experts or amateurs. FIG. 5 shows a scenario 540 in which a user U is also a coach C. A content module can be stored in a database 525 in communicative link with the application server 520 or the content module can be stored locally on a coach's database 530.

Payment may be required to receive content modules or the content modules can be free. In one embodiment, a user chooses a coach and subscribes to the coach's program to access the content modules distributed by the coach. When payment or subscription is required, the application server 520 can manage the subscription and payment services. The subscribed content modules are pushed to the user, who may bookmark the module. Optionally, a coach may view a user's progress based on the bookmarked modules and scored properties against the bookmarked modules. The coach may also communicate with the subscribing user.

As one of ordinary skill in the art will appreciate, various changes, substitutions, and alterations could be made or otherwise implemented without departing from the principles of the present invention, e.g. the Internet could be substituted by a local area network and the content modules can include any type of content. Accordingly, the scope of the invention should be determined by the following claims and their legal equivalents.

What is claimed is:

1. A method for tracking user property scores against content modules, comprising:
   (a) having a computer implemented social network of a plurality of users, wherein each of said plurality of users of said social network is (i) associated with one or more user properties selected from the group consisting of a behavioral action of said user and an emotional state of the user and (ii) trying to improve at least one personal aspect;
   (b) having a plurality of content modules comprising at least one module with coaching content for personal behavioral modification sought by one or more of said plurality of users, wherein (i) said plurality of content modules are accessible by said plurality of users of said social network and (ii) each of said plurality of content modules is related to one or more of said user properties;
   (c) allowing said plurality of users of said social network to access a bookmark function, wherein said bookmark function enables each of said users of said social network (i) to generate a direct link to at least one of said plurality of content modules containing the coaching content for the personal behavioral modification sought by each of said users and (ii) to store the direct link as part of a respective collection of direct links which are stored on a computer of each of said users and managed by each of said users;
   (d) allowing each of said users having a bookmarked content module to access a scoring function for said bookmarked content module, wherein
      said scoring function allows each of said users having said bookmarked content module to score themselves multiple times with regard to said one or more user properties related to said bookmarked content module independently of said social network,
      said multiple scores of each of said users indicate an assessment by said user of how well said user views themselves as having followed coaching content in said bookmarked content module,
      said multiple scores of each of said users are made over a period of time, and
      each of said plurality of content modules comprises an embedded respective scoring instruction describing a binary or numerical range scoring metric to be used by each of said users to score themselves with regard to at least one of said user properties against the content module in which said respective scoring instruction is embedded;
   (e) tracking said multiple scores provided by each of said users over at least a subset of said period of time;
   (f) automatically forming an online community comprising a plurality of members who have all bookmarked said bookmarked content module and have similar goals with respect to the coaching content of said bookmarked module, wherein each of said plurality of members can view a list of the other members of the online community and the scores of the other members of the online community; and
   (g) maintaining a user profile for each of said plurality of users of said social network, wherein said user profile comprises a "tip of the day" comprising a posting of one of said plurality of content modules.

2. A system for tracking user property scores against content modules, comprising:
   (a) an application server for operating a computer implemented social network of a plurality of users, wherein each of said plurality of users of said social network is (i) associated with one or more user properties selected from the group consisting of a behavioral action of said user and an emotional state of the user and (ii) trying to improve at least one personal aspect;
   (b) a database for storing a plurality of content modules comprising at least one module with coaching content for personal behavioral modification sought by one or more of said plurality of users, wherein (i) said plurality of content modules are accessible by said plurality of users of said social network and (ii) each of said plurality of content modules is related to one or more of said user properties;
   (c) a bookmarking function allowing each of said users of said social network to (i) to generate a direct link to at least one of said plurality of content modules containing the coaching content for the personal behavioral modification sought by each of said users and (ii) to store the direct link as part of a respective collection of direct links which are stored on a computer of each of said users and managed by each of said users;
   (d) a scoring function accessible by each of said users having a bookmarked content module wherein,
      said scoring function allows each of said users having said bookmarked content module to score themselves multiple times with regard to said one or more user properties related to said bookmarked content module independently of said social network,
      said scores of each of said users indicate an assessment by said user of how well said user views themselves as having followed coaching content in said bookmarked content module,
      said scores are tracked over a period of time, and
      each of said plurality of content modules comprises an embedded respective scoring instruction describing a binary or numerical range scoring metric to be used by each of said users to score themselves with regard to at least one of said user properties against the content module in which said respective scoring instruction is embedded;
   (e) a tracking function for tracking said multiple self-assessment scores provided by each of said users over at least a subset of said period of time;
   (f) a community function configured to automatically form an online community comprising a plurality of members who have all bookmarked said bookmarked content module and have similar goals with respect to the coaching content of said bookmarked module, wherein each of said plurality of members can (i) view a list of the other members of the online community and (ii) view the tracked scores of the other members of the online community; and (g) wherein said application server maintains a user profile for each of said plurality of users of said social network, wherein said user profile comprises a "tip of the day" comprising a posting of one of said plurality of content modules.

\* \* \* \* \*